United States Patent
Rudolf et al.

(10) Patent No.: US 12,286,416 B2
(45) Date of Patent: *Apr. 29, 2025

(54) METHOD FOR THE PREPARATION OF THIOCARBONATES

(71) Applicant: BASF SE, Ludwigshafen am Rhein (DE)

(72) Inventors: Peter Rudolf, Ludwigshafen (DE); Indre Thiel, Ludwigshafen (DE); Thomas Maximilian Wurm, Ludwigshafen (DE); Joaquim Henrique Teles, Ludwigshafen (DE); Jan-Dirk Arndt, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 957 days.

This patent is subject to a terminal disclaimer.

(21) Appl. No.: 17/423,518

(22) PCT Filed: Jan. 17, 2020

(86) PCT No.: PCT/EP2020/051110
§ 371 (c)(1),
(2) Date: Jul. 16, 2021

(87) PCT Pub. No.: WO2020/148421
PCT Pub. Date: Jul. 23, 2020

(65) Prior Publication Data
US 2022/0073492 A1  Mar. 10, 2022

(30) Foreign Application Priority Data

Jan. 18, 2019 (EP) ..................................... 19152436

(51) Int. Cl.
C07D 327/04 (2006.01)
(52) U.S. Cl.
CPC .................................. C07D 327/04 (2013.01)
(58) Field of Classification Search
CPC .................................................. C07D 327/04
See application file for complete search history.

(56) References Cited

U.S. PATENT DOCUMENTS

| | | |
|---|---|---|
| 2,828,318 A | 3/1958 | Reynolds |
| 3,072,676 A | 1/1963 | Johnson et al. |
| 3,201,416 A | 8/1965 | Johnson et al. |
| 3,349,100 A | 10/1967 | Villa |
| 3,517,029 A | 6/1970 | Johnson |
| 4,111,933 A | 9/1978 | Eckert et al. |
| 11,518,752 B2 * | 12/2022 | Thiel ............. C07D 327/04 |
| 2020/0354333 A1 | 11/2020 | Rudolf et al. |

FOREIGN PATENT DOCUMENTS

| | | |
|---|---|---|
| EP | 2468791 A1 | 6/2012 |
| WO | 2016/022408 | 2/2016 |
| WO | WO-2019/034469 A1 | 2/2019 |

OTHER PUBLICATIONS

Carceller, et al., "Synthesis and structure-activity relationships of 1-acyl-4-((2-methyl-3-pyridyl)cyanomethyl)piperazines as PAF antagonists", Journal of Medicinal Chemistry, vol. 36, Issue 20, Oct. 1, 1993, pp. 2984-2997.
International Search Report for PCT Patent Application No. PCT/EP2020/051110, Issued on Mar. 9, 2020, 4 pages.
Kihara, et al., "Preparation of 1,3-Oxathiolane-2-thiones by the Reaction of Oxirane and Carbon Disulfide", The Journal of Organic Chemistry, vol. 60, Issue 2, Jan. 1, 1995, pp. 473-475.
Luo, et al., "Synthesis of cyclic monothiocarbonates via the coupling reaction of carbonyl sulfide (COS) with epoxides", Catalysis Science & Technology, vol. 6, Issue 1, Aug. 13, 2015, pp. 188-192.
Nishiyama, et al., "A facile method for the synthesis of 1,3-oxathiolan-2-ones by reaction of oxiranes, sulfur, and carbon monoxide", Tetrahedron, vol. 62, Issue 24, Jun. 12, 2006, pp. 5803-5807.
Reynolds, et al., "Mercaptoethylation. IV. Preparation and Some Reactions of Alkyl 2-Hydroxyethylthiolcarbonates", The Journal of Organic Chemistry, vol. 26, Issue 12, Dec. 1, 1961, pp. 5119-5122.
Taguchi, et al., "The Reaction of Oxiranes with Carbon Disulfide under High Pressure", Bulletin of the Chemical Society of Japan, vol. 61, Issue 3, Mar. 1988, pp. 921-925.
Wang, et al., "Cooperative catalysis with binary Lewis acid—Lewis base system for the coupling of carbon disulfide and epoxides", Applied Organometallic Chemistry, vol. 26, Issue 11, Sep. 20, 2012, pp. 614-618.
Yin, et al., "Bis-aryl Urea Derivatives as Potent and Selective LIM Kinase (Limk) Inhibitors", Journal of Medicinal Chemistry, vol. 58, Issue 4, Jan. 26, 2015, pp. 1846-1861.
U.S. Appl. No. 16/639,339, filed Feb. 14, 2020, 2020/0354333, Rudolf et al.
Liu et al., "Potassium Thioacids Mediated Selective Amide and Peptide Constructions Enabled by Visible Light Photoredox Catalysis", ACS Catalysis, vol. 6, Feb. 8, 2016, pp. 1732-1736, with supporting information, pp. 1-53.

* cited by examiner

*Primary Examiner* — Laura L Stockton
(74) *Attorney, Agent, or Firm* — Grüneberg and Myers PLLC

(57) ABSTRACT

Provided is a process for the preparation of a compound with at least one five-membered cyclic monothiocarbonate group. A compound C1 with at least one halohydrin group is used as starting material. Compound C1 is reacted with phosgene or an alkyl chloroformate to give an adduct C2. The adduct C2 is reacted with a compound that includes anionic sulfur to obtain the compound with at least one five-membered cyclic monothiocarbonate group.

12 Claims, No Drawings

METHOD FOR THE PREPARATION OF THIOCARBONATES

CROSS-REFERENCE TO RELATED APPLICATIONS

This application is a National Stage entry under § 371 of International Application No. PCT/EP2020/051110, filed on Jan. 17, 2020, and which claims the benefit of European Application No. EP19152436.2, filed on Jan. 18, 2019. The content of each of these applications is hereby incorporated by reference in its entirety.

BACKGROUND OF THE INVENTION

Field of the Invention Description

Object of the present invention is a process for the preparation of a compound with at least one five-membered cyclic monothiocarbonate group, wherein
 a) a compound C1 with at least one halohydrin group is used as starting material,
 b) compound C1 is reacted with phosgene or an alkyl chloroformate to give an adduct C2, and
 c) the adduct C2 is reacted with a compound comprising anionic sulfur to obtain the compound with at least one five-membered cyclic monothiocarbonate group.

Description of Related Art

Cyclic monothiocarbonates are useful starting materials for the synthesis of chemical compounds. So far, however, cyclic monothiocarbonates have not been used in any industrial processes in significant amounts.

Different methods for the synthesis of cyclic monothiocarbonates are described in the state of the art.

According to the process disclosed in U.S. Pat. No. 3,349,100 alkylene monothiocarbonates are obtained by reacting an epoxide with carbonyl sulfide. The availability of carbonyl sulfide is limited. Yields and selectivities of alkylene monothiocarbonates obtained are low.

A synthesis using phosgene as starting material is known from U.S. Pat. No. 2,828,318. Phosgene is reacted with hydroxymercaptanes. Yields of monothiocarbonates are still low, and by-products from polymerization are observed.

Object of U.S. Pat. Nos. 3,072,676 and 3,201,416 is a two-step-process for the preparation of ethylene monothiocarbonates. In a first step mercaptoethanol and chlorocarboxylates are reacted to give hydroxyethylthiocarbonate, which is heated in the second step in the presence of a metal salt catalyst to form the ethylene monothiocarbonate.

According to U.S. Pat. No. 3,517,029 alkylene monothiocarbonates are obtained by reacting mercaptoethanol and a carbonate diester in the presence of a catalytically active salt of thorium.

Yoichi Taguchi et al., Bull. Chem. Soc. Jpn., 1988, 61, 921-925 disclose the formation of monothiocarbonate by reacting carbon disulfide and 2,2-dimethyloxirane in the presence of trimethylamine.

Yutaka Nishiyama et al., Tetrahedron, 2006, 62, 5803-5807 disclose the formation of monothiocarbonate using epoxide, sulfur and carbon monoxide as reactants in the presence of sodium hydride.

M. Luo, X.-H. Zhang and D. J. Darensbourg, Catalysis Science & Technology, 2015, article accepted on Aug. 13, 2015 (DOI: 10.1039/c5cy00977d) disclose some specific cyclic monothiocarbonates obtained via coupling reaction of carbonyl sulfides with epoxides.

Yi-Ming Wang, Bo Li, Hui Wang, Zhi-Chao Zhang and Xiao-Bing Lu, Appl. Organometal. Chem. 2012, 26, 614-618 also disclose some specific cyclic monothiocarbonates obtained via coupling reaction of carbonyl sulfides with epoxides.

The object of EP-A-2468791 are epoxy compositions that comprise compounds with a five membered cyclic ring system comprising oxygen and sulfur. The compounds disclosed in EP-A 2468791 and in N. Kihara et al., J. Org. Chem. 1995, 60, 473-475 cited in EP-A-2468791, are compounds with five membered cyclic ring systems comprising at least 2 sulfur atoms. Compounds with one sulfur atom are not mentioned.

WO 2019/034469 A1 relates to a process for the synthesis of a compound with at least one cyclic monothiocarbonate group by reacting a compound with at least one epoxy group with phosgene and subsequently reacting the adduct obtained with an anionic sulfur compound.

None of the processes described above has gained industrial importance due to their deficiencies. Many of these processes involve the use of starting materials of low availability, high costs or problematic properties. Furthermore, yields and selectivities, in particular selectivity of structural isomers, obtained are not yet satisfying for production on industrial scale. As a consequence, the availability of thiocarbonates in commercial quantities is low even though thiocarbonates are of high interest as intermediates in chemical synthesis.

Hence, it was an object of this invention to provide a process to produce thiocarbonates which is useful for industrial scale production. The process should not involve expensive starting materials or starting materials of low availability. The process should be easy to perform, should be as economic as possible and give thiocarbonates in high yield and selectivity.

SUMMARY OF THE INVENTION

Accordingly, a process for the preparation of a compound with at least one five-membered cyclic monothiocarbonate group has been found.

The invention relates to a process for the preparation of a compound with at least one five-membered cyclic monothiocarbonate group, wherein
 a) a compound C1 with at least one halohydrin group is used as starting material,
 b) compound C1 is reacted with phosgene or an alkyl chloroformate to give an adduct C2, and
 c) the adduct C2 is reacted with a compound comprising anionic sulfur to obtain the compound with at least one five-membered cyclic monothiocarbonate group.

DETAILED DESCRIPTION OF THE INVENTION

A five-membered cyclic monothiocarbonate group is a ring system with 5 members, three of them are from the monothiocarbonate —O—C(=O)—S— and the further two members are carbon atoms closing the five-membered cycle.
To The Process
a) Halohydrin Compounds Starting compound for the process is a compound C1 with at least one halohydrin group.

A halohydrin group is a group of two vicinal carbon atoms, one is substituted by a hydroxy group, the other by a halide (OH—C—C—H, with H being a halide).

The term "halide", as used herein, is the trivial name of a covalently bonded halogen atom.

Preferably, the halohydrin group is a chlorohydrin group.

Compounds with halohydrin groups may be obtained by halogenation, preferably chlorination of compounds with alcohol groups. An example is the chlorination of glycerol to a compound with two chloride groups resulting in a compound of formula Cl—CH₂—HCOH—CH₂—Cl or Cl—CH₂—HCCl—CH₂—OH or mixtures thereof.

Another method to produce halohydrins is the oxidation of olefins with an oxidant comprising a halogen. An example is the oxidation of carbon/carbon double bonds with hypochlorite (ClO⁻) resulting in a chlorohydrin group.

Furthermore, a compound with at least one hydroxy group may be reacted with epichlorohydrin (EPI) to give preferably the following chlorohydrin:

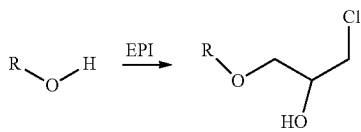

Compound C1 may be a compound with only one halohydrin group, such compounds are usually low molecular weight compounds with a molecular weight below 5000 g/mol, in particular below 1000 g/mol, more specifically below 500 g/mol.

A compound with one halohydrin group is, for example, 2-chloroethanol, 2-chloro-1-propanol, 2,3-dichloro-1-propanol, 1-chloro-2-methyl-2-propanol.

Compound C1 may comprise more than one halohydrin group. Such compounds C1 are obtainable from compounds with more than one hydroxy group or with more than one ethylenically unsaturated carbon-carbon group by transferring these groups into halohydrin groups as described above. Polymeric compounds C1 may have a number average molecular weight Mn of, for example, up to 2.000.000, notably of up to 500.000, as determined by GPC against polystyrene as standard.

Compounds C1 may comprise, for example, up to 1000, in particular up to 500, preferably up to 100 halohydrin groups, preferably chlorohydrin groups.

In a preferred embodiment, compound C1 is a compound with 1 to 100, more preferably 1 to 10 and in a most preferred embodiment with 1 to 3, notably 1 or 2 halohydrin groups, preferably chlorohydrin groups.

b) First Process Step, Formation of Adduct

In the first process step compound C1 is reacted with phosgene or an alkyl chloroformate to give an adduct C2. Preferably, it is reacted with phosgene. The word phosgene shall include any phosgene substitutes; phosgene substitutes are compounds that set free phosgene. A phosgene substitute is, for example, triphosgene.

Below the reaction of step b) is shown exemplarily for a specific compound C1 with one chlorohydrin group and phosgene as reactants.

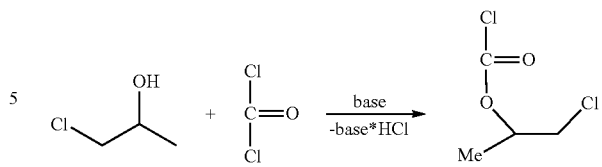

Alternatively preferred is the first process step, wherein compound C1 is reacted with an alkyl chloroformate. Below the reaction of step b) is shown exemplarily for a specific compound C1 with one chlorohydrin group and an alkyl-chloroformate as reactants.

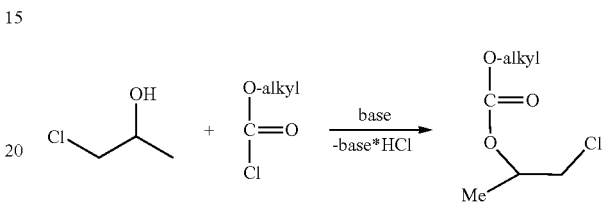

Compound C1 may be reacted with phosgene or an alkyl chloroformate in any stochiometric ratio. Preferably, a very high excess of compound C1 is avoided, as such a high excess would result in high amounts of unreacted starting compounds which would have to be removed during work-up of the obtained product composition. Preferably, the conversion is performed in the presence of a base such as a tertiary amine.

Preferably, the phosgene, respectively chloroformate, is used in an amount of 0.1 to 5 mol, in particular of 0.5 to 2 mol per mol of each halohydrin group of compounds C1. In a particularly preferred embodiment the phosgene, respectively chloroformate, is used in excess.

With at least equimolar amounts of phosgene, respectively chloroformate, halohydrin groups that remain unreacted, can be avoided. Hence, in a preferred embodiment the phosgene, respectively chloroformate, is used in an amount of 0.9 to 5 mol, more preferably of 1 to 2 mol, in particular 1 to 1.5 mol per mol of each halohydrin group of compound C1.

The phosgene and the chloroformate are preferably a compound of formula (II)

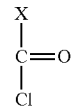

wherein X is Cl in case of phosgene or a group O—R⁵ with R⁵ representing a $C_1$-$C_4$-alkyl group in case of chloroformate.

In a preferred embodiment compound C1 is reacted with phosgene.

In the reaction HCl is set free.

Therefore, the reaction is preferably performed in the presence of a base as, for example, tertiary amines to form a salt of the hydrohalogenic acid which can be isolated from the reaction mixture.

Compound C1 is preferably added to phosgene or alkyl chloroformate. As the reaction is exothermic, the addition is preferably made slowly so that the temperature of the reaction mixture is kept at the desired value. Preferably, the reaction mixture is cooled during the addition.

Preferably, the temperature of the reaction mixture is kept at −40 to 60° C., notably at 5 to 50° C.

Low molecular compounds C1 are usually liquid; hence, an additional solvent is not required. Preferably, a solvent is used in case of compounds C1 that are solid at 21° C. Suitable solvents are notably aprotic solvents, such as hydrocarbons, including aromatic hydrocarbons and chlorinated hydrocarbon, for example, toluene, chloro-benzene or dichloro-benzene.

A preferred solvent for a solid compound C1 is an additional liquid compound C1. The liquid compound C1 together with the solid compound C1 undergo the reaction as described in process steps b) and c). The cyclic monothiocarbonate obtained from the liquid compound would usually be liquid as well and, therefore, would serve also as solvent for the most probably solid monothiocarbonate obtained from the solid compound with at least one halohydrin group.

When the reaction is completed, unreacted phosgene or chloroformate may be removed from the mixture by distillation. The product mixture obtained comprises a compound C2 with at least one β-halo-alkylchloroformate group (in case of phosgene) or at least one β-halo-carbonate group (in case of using an alkyl chloroformate). The next process step may follow immediately.

The terms "compound C2" and "adduct C2" are used herein interchangeably and have the same meaning.

The process step b) is preferably performed with phosgene.

Accordingly, in a preferred aspect, the invention relates to a process for the preparation of a compound with at least one five-membered cyclic monothiocarbonate group, wherein
a) a compound C1 with at least one halohydrin group is used as starting material,
b) compound C1 is reacted with phosgene to give an adduct C2, and
c) the adduct C2 is reacted with a compound comprising anionic sulfur to obtain the compound with at least one five-membered cyclic monothiocarbonate group.

More preferably, compound C1 with at least one chlorohydrin group is used as starting material.

c) Second Process Step, Formation of the Cyclic Monothiocarbonate Groups

The second process step c) can be exemplarily shown for $Na_2S$ and β-chloro-alkylchloroformate as reactants as follows:

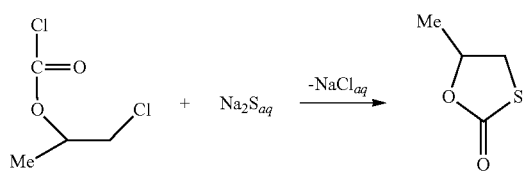 [SMILES: CC(CCl)OC(=O)Cl ; CC1CSC(=O)O1]

In case of using phosgene in the process step b) the process step c) is usually a one-step process.

In case of using an alkyl chloroformate in the process step b) the process step c) is understood to be a two-step process. Either the chloro atom or the O-alkyl group may be substituted by the SH group, followed by a ring closure step to form the cyclic monothiocarbonate.

A solvent may be added in step c). Suitable solvents are, in particular, aprotic solvents. Suitable solvents are, for example, hydrocarbons, including aromatic hydrocarbons and chlorinated hydrocarbon or hydrophilic aprotic solvents, for example, ethers such as tetrahydrofuran, dioxane, polyether such as glymes, acetonitrile or dimethylsulfoxide.

The product mixture from step b) is reacted with a compound comprising anionic sulfur. The compound comprising anionic sulfur is preferably a salt.

The anionic sulfur is preferably $S^{2-}$, a polysulfide of formula $(S_p)^{2-}$ with p being an integral number from 2 to 200, preferably from 2 to 10 or $HS^{1-}$.

The cation of the salt may be any organic or inorganic cation. Preferably, it is an inorganic cation, in particular a metal. Usual metal cations are, for example, cations of alkali or earth alkali metals, such as sodium or potassium.

Preferred salts are $Na_2S$, $K_2S$, NaSH or KSH or any hydrates thereof.

The salt may be used in combination with a basic compound, in particular a metal hydroxide, such as, in particular, NaOH or KOH. Such an additional basic compound is preferably used in case of salts with $SH^-$ as anion.

The anionic sulfur may also be generated in situ, starting from sulfur or a compound comprising sulfur in non-ionic form. For example, $H_2S$ may be used as source for anionic sulfur. In the presence of a basic compound, for example, NaOH (see above), anionic sulfur is obtained from $H_2S$ in situ.

The salt with anionic sulfur, respectively the compound from which anionic sulfur is generated in situ (together referred herein as the sulfur compound), is preferably added to the product mixture obtained in b). The sulfur compound may be added as such or, for example, as a solution in a suitable solvent, such as water. In a preferred embodiment of the invention, the sulfur compound is dissolved in a solvent, in particular water, and the solution is added.

If the sulfur compound is added as a solution in water, a two-phase system comprising an organic and an aqueous phase is obtained, and the reaction occurs in such two-phase system. If a one-phase system is desired instead, a suitable solvent may be added which acts as intermediary to combine the aqueous and organic phase to one phase again. A suitable solvent may be a hydrophilic aprotic solvent, for example, a hydrophilic aprotic solvent listed above.

As the reaction is exothermic as well, addition of the salt, respectively the solution of the salt, is preferably made slowly so that the temperature of the reaction mixture is kept at the desired value. Preferably, the reaction mixture is cooled during the addition.

Preferably, the temperature of the reaction mixture is kept at −40 to 60° C., notably at −10 to 50° C.

In case of using an alkylchloroformate, the ring closure step, i.e., after the addition of the salt, is generally done at room temperature or at elevated temperatures, for example, from 60 to 140° C., preferably from 70 to 120° C.

The reactants may be added or combined in any order. For example, the sulfur compound may be added to compound C2, or compound C2 may be added to the compound comprising anionic sulfur.

Preferably, the salt is added in an amount of 0.5 to 2.0 mol per mol of each β-chloro-alkylchloroformate group of compounds C2, respectively β-halo-alkylchloroformate of compounds C2.

Preferably, the salt is added in an amount of 1.0 to 2.0 mol per mol of each β-chloro-alkylchloroformate group of compounds C2, respectively β-halo-alkylchloroformate of compounds C2.

In a most preferred embodiment, the salt is added in an amount of 1.0 to 1.3 mol per mol of each β-chloro-alkylchloroformate group of compounds C2, respectively β-haloalkylchloroformate of compounds C2, as no significant excess of the salt is required to get a quick and complete reaction of all β-chloro-alkylchloroformate groups, respectively 3-halo-alkylchloroformate groups.

By reaction with the salt the β-halo-alkylchloroformate groups are transferred into five-membered cyclic monothiocarbonate groups. The five-membered ring system is formed from three carbon atoms, one oxygen and one sulfur with a further oxygen double bonded to the carbon atom which is located between the oxygen and the sulfur of the ring system.

If desired, the second process step may be performed in the presence of a catalyst. Such a catalyst is, for example, a phase transfer catalyst such as ammonium salts, heterocyclic ammonium salts and phosphonium salts.

In case of using an alkylchloroformate in step b), the ring closure step may be performed with a catalyst, for example, an acid catalyst such as p-toluene sulfonic acid or methanesulfonic acid.

The final product obtained under c) may be worked up by extracting with a hydrophilic solvent, preferably water. In case that the above salt of anionic sulfur has been used in form of an aqueous solution no further water may be required. The organic and aqueous phases are separated. The organic phase may be washed with water which has preferably a pH of 4 to 10, in particular a pH of at least 7. The organic phase comprises the compound with at least one cyclic monothiocarbonate group. The aqueous phase comprises unreacted sulfide/hydrogen-sulfide salt and/or $Na^+Hal^-$, e.g., NaCl, and at least partially any catalyst added.

Any solvent may be removed from the organic phase by distillation. The obtained compound with at least one cyclic monothiocarbonate group may be further purified by distillation or may be used without further purification.

Hence, compounds with at least one five-membered cyclic monothiocarbonate group are obtained by the above process.

To the Preparation of a Compound with One Five-Membered Cyclic Monothiocarbonate Group A preferred process for the preparation of a compound with one five-membered cyclic monothiocarbonate group comprises a) Compound C1 of Formula (Ia)

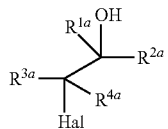

wherein $R^{1a}$ to $R^{4a}$ independently from each other represent hydrogen or an organic group with at maximum 50 carbon atoms whereby alternatively, $R^{2a}$, $R^{4a}$ and the two carbon atoms of the halohydrin group may also together form a five to ten membered carbon ring and Hal representing a halide, is used as starting material, b) Compound C1 is Reacted with a Compound of Formula (II)

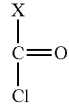

wherein X is Cl (phosgene) or a group $O—R^5$ with $R^5$ representing a $C_1$-$C_4$-alkyl group (chloroformate) to give an adduct of formula (IIIa)

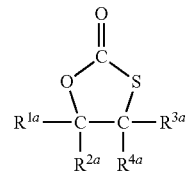

wherein $R^{1a}$ to $R^{4a}$ have the meaning above, and c) Reacting the Adduct of Formula (IIIa) with a Compound Comprising Anionic Sulfur to the Cyclic Monothiocarbonate of Formula (IVa)

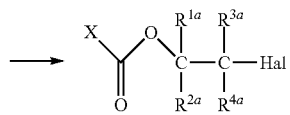

wherein $R^{1a}$ to $R^{4a}$ have the meaning above.

Hal may be fluoride, chloride, bromide or iodide. Preferably Hal represents chloride.

In case that any of $R^{1a}$ to $R^{4a}$ represent an organic group, such organic group is preferably an organic group with up to 30 carbon atoms. Preferably, $R^{2a}$, $R^{4a}$ and the two carbon atoms of the halohydrin group do not form a five to ten membered carbon ring.

In case that any of $R^{1a}$ to $R^{4a}$ represent an organic group, such organic group may comprise other elements than carbon and hydrogen. In particular, it may comprise oxygen, nitrogen, sulfur and chloride. In a preferred embodiment the organic group may comprise oxygen or chloride. $R^{1a}$ to $R^{4a}$ may comprise oxygen, for example, in form of ether, hydroxy, aldehyde, keto or carboxy groups.

Preferably, at least one of $R^{1a}$ to $R^{4a}$ in formula (Ia) and accordingly in formulae (IIIa) and (IVa) is not hydrogen.

More preferably, two and/or three of $R^{1a}$ to $R^{4a}$ in formula (Ia) and accordingly in formulae (IIIa) and (IVa) represent hydrogen, and the remaining groups $R^{1a}$ to $R^{4a}$ represent an organic group.

Most preferably, three of $R^{1a}$ to $R^{4a}$ in formula (Ia) and accordingly in formulae (IIIa) and (IVa) represent hydrogen, and the remaining group of $R^{1a}$ to $R^{4a}$ represents an organic group.

In a preferred embodiment, $R^{1a}$ or $R^{2a}$ is the remaining group representing an organic group.

In a preferred embodiment, the remaining groups or the remaining group represent a group $CH_2$—Cl, $CH_2$—Y—$R^6$ or $CH_2$—O—C(=O)—$R^7$ or $CH_2$—$NR^8R^9$ with $R^6$ to $R^9$ being an organic group with up to 30 carbon atoms, preferably up to 20 carbon atoms and Y being O or S.

In particular, $R^6$ and $R^7$ represent an aliphatic, cycloaliphatic or aromatic group, which may comprise oxygen, for example, in form of ether groups. In a preferred embodiment, $R^6$ to $R^7$ represent a linear or branched alkyl group, alkoxy group, polyalkoxy group or alkenyl group. In a most preferred embodiment, $R^6$ to $R^9$ represent a linear or branched alkyl group or alkenyl group.

In particular, $R^8$ and $R^9$ represent an aliphatic, cycloaliphatic or aromatic group, which may comprise oxygen, preferably in form of carbonyl groups. In a preferred embodiment, $R^8$ represents a group $C(=O)—R^{10}$, and $R^9$ represents a group $C(=O)—R^{11}$ resulting in a group

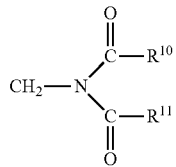

$R^{10}$ and $R^{11}$ independently from each other represent a hydrocarbon group, which may be an aliphatic, cycloaliphatic or aromatic group or, alternatively, $R^8$ and $R^9$ together form an aliphatic or aromatic ring system.

As preferred compounds with one five-membered cyclic monothiocarbonate group obtained by the process may be mentioned:

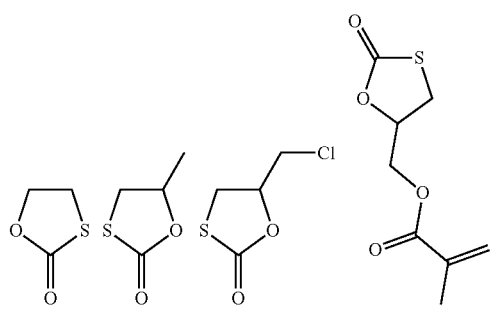

All disclosure in this patent application relating to process steps b) and c) apply to the above preparation of a compound with one five-membered cyclic monothiocarbonate group.

Processes for the production of cyclic monothiocarbonates known from the prior art usually give mixtures of structural isomers. With the process of this invention the content of structural isomers is avoided.

To the preparation of a compound with more than one five-membered cyclic monothiocarbonate group A preferred process relating to the preparation of a compound with more than one five-membered cyclic monothiocarbonate group comprises
a) A Compound C1 of Formula (Ib)

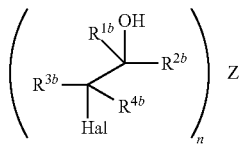

with $R^{1b}$ to $R^{4b}$ independently from each other representing hydrogen or an organic group with up to 50 carbon atoms whereby, alternatively, $R^{2b}$, $R^{4b}$ and the two carbon atoms of the epoxy group may also together form a five to ten membered carbon ring and one of the groups $R^{1b}$ to $R^{4b}$ is a linking group to Z, Hal representing an halide, n representing an integral number of at least 2 and Z representing a n-valent organic group, is used as starting material,
b) The Compound is Reacted with a Compound of Formula (II)

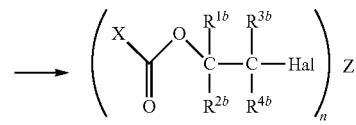

wherein X is Cl or a group $O—R^5$ with $R^5$ representing a $C_1$-$C_4$-alkyl group, to give an adduct of formula (IIIb)

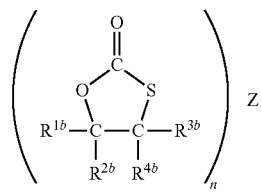

wherein $R^{1b}$ to $R^{4b}$, Z, Hal and n have the meaning above, and
c) The Adduct of Formula (IIIb) is Reacted with a Compound Comprising Anionic Sulfur to a Compound of Formula (IVb) Comprising at Least Two Monothiocarbonate Groups wherein $R^{1b}$ to $R^{4b}$, Z and n have the meaning above.

Hal may be fluoride, chloride, bromide or iodide. Preferably, Hal represents chloride.

In case that any of $R^{1b}$ to $R^{4b}$ represent an organic group, such organic group is preferably an organic group with up to 30 carbon atoms. In a further preferred embodiment, $R^{2b}$ and $R^{4b}$ do not form a five to ten membered carbon ring together with the two carbon atoms of the halohydrin group.

In case that any of $R^{1b}$ to $R^{4b}$ represent an organic group, such organic group may comprise other elements than carbon and hydrogen. In particular, it may comprise oxygen, nitrogen, sulfur and chloride. In a preferred embodiment, the organic group may comprise oxygen or chloride. $R^{1b}$ to $R^{4b}$ may comprise oxygen, for example, in form of ether, hydroxy, aldehyde, keto or carboxy groups.

One of the groups $R^{1b}$ to $R^{4b}$ is the linking group to Z.

Preferably, the linking group is simply a bond or a group $CH_2—$, $CH_2—Y—$ with Y being O or S, or a group $CH_2—O—C(=O)—$ or $CH_2—NR^{20}—$ with $R^{20}$ being an aliphatic group, in particular an alkyl group with at maximum 20 carbon atoms, or a group $C(=O)—O—$ or a group $R^{21}—C(=O)—O—$, wherein $R^{21}$ is an organic group, preferably a hydrocarbon group with up to 20 carbon atoms.

More preferably, the linking group is simply a bond or a group $CH_2—$, a group $CH_2—O—$ or a group $CH_2—O—C(=O)—$.

In a most preferred embodiment, the linking group is a group $CH_2—O—$.

Preferably, two or three of the groups $R^{1b}$ to $R^{4b}$ in formula (Ib) and accordingly in formulae (IIIb) and (IVb) are hydrogen.

In a most preferred embodiment, three of the groups $R^{1b}$ to $R^{4b}$ represent hydrogen, and the remaining group of $R^{1b}$ to $R^{4b}$ is the linking group to Z.

In a most preferred embodiment, groups $R^{1b}$ or $R^{2b}$ is the linking group to Z.

With the linking groups $CH_2$—O— or $CH_2$—O—C(=O)— and with the preferred embodiment that three of $R^{1b}$ to $R^{4b}$ are hydrogen, the group in the bracket of formula (Ib) becomes a halohydrin ether group of formula

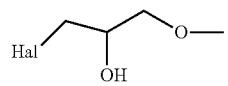

or a halohydrinester group of formula

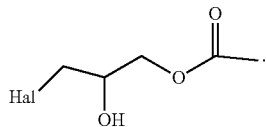

In a most preferred embodiment, the group in the bracket of formula (Ib) is the above halohydrin-ether group or halohydrin ester group.

In the embodiment that $R^{2b}$ and $R^{4b}$ do form a five to ten membered carbon ring together with the two carbon atoms of the halohydrin group, the linking groups mentioned above may alternatively be bonded to the carbon atoms of the ring system.

n represents an integral number of at least 2. For example, n may be an integral number from 2 to 1000, in particular from 2 to 100 respectively 2 to 10.

In a preferred embodiment, n is an integral number from 2 to 5, in particular n is 2 or 3.

In a most preferred embodiment, n is 2.

Z represents a n-valent organic group. In case of a high number of n, such as, for example, 10 to 1000, Z may be a polymeric backbone of a polymer obtained, for example, by polymerization or copolymerization, such as radical polymerization of ethylenically unsaturated momomers, polycondensation or polyaddition. For example, polymers like polyesters or polyamides are obtained via polycondensation under elimination of water or alcohol and, for example, polyurethanes or polyureas are obtained via polyaddition.

Compounds of formula (Ib) are, for example, oligomers/polymers with halohydrin groups obtained by addition of epichlorohydrin to polymers bearing hydroxy and/or carboxy functionalities. Compounds of formula (Ib) are, for example, polymers with halohydrin groups obtained by condensation reaction of epichlorohydrin with oligomers/polymers bearing imido functionalities.

In a preferred embodiment, Z is a n-valent organic group with up to 50 carbon atoms, in particular up to 30 carbon atoms, and which may comprise other elements than carbon and hydrogen and n is an integral number from 2 to 5, notably 2 or 3, most preferred 2.

In a particularly preferred embodiment, Z is a n-valent organic group with up to 50 carbon atoms, in particular up to 30 carbon atoms, and which comprises carbon, hydrogen and optionally oxygen, only and no further elements and n is an integral number from 2 to 5, notably 2 or 3, most preferred 2.

In a preferred embodiment, Z is a polyalkoxylene group of formula (G1)

$$(V\text{—}O\text{—})_m V$$

wherein V represents a $C_2$-$C_{20}$-alkylene group, and m is an integral number of at least 1.

Preferably, the $C_2$-$C_{20}$-alkylene group is a $C_2$-$C_4$-alkylene group, in particular ethylene or propylene. m may, for example, be an integral number from 1 to 100, in particular from 1 to 50. The terminal alkylene groups V are bonded to the linking group, which is one of the groups $R^{1b}$ to $R^{4b}$, see above.

In a further preferred embodiment, Z is a group of formula (G2)

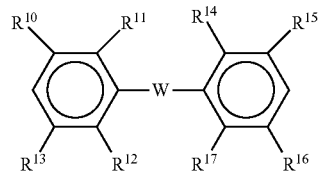

wherein W is a bi-valent organic group with at maximum 10 carbon atoms, and n is 2, and $R^{10}$ to $R^{17}$ independently from each other represent H or a C1- to C4 alkyl group. Preferably, at least six of $R^{10}$ to $R^{17}$ are hydrogen. In a most preferred embodiment, all of $R^{10}$ to $R^{17}$ are hydrogen.

The two hydrogen atoms in the para position to W are replaced by the bond to the linking group, which is one of the groups $R^{1b}$ to $R^{4b}$, see above.

Groups W are, for example:

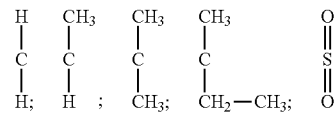

Preferably, W is an organic group that consists of carbon and hydrogen, only.

Most preferred W is

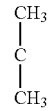

which corresponds to the structure of bisphenol A.

In a further preferred embodiment, Z is a group G3, wherein G3 represents an alkylene group, notably a $C_2$-$C_8$-alkylene group; preferred examples of such an alkylene group are ethylene ($CH_2$—$CH_2$), n-propylene ($CH_2$—$CH_2$—$CH_2$) and notably n-butylene ($CH_2$—$CH_2$—$CH_2$—$CH_2$).

Examples for preferred compounds with more than one five-membered cyclic monothiocarbonate group are in particular those which are obtained by transferring all halohydrin groups of the halohydrin compounds into five-membered cyclic monothiocarbonate groups.

The present invention provides for a very economic and effective process for the production of compounds with at least one five-membered cyclic monothiocarbonate group. The process is suitable for industrial scale production. The process does not involve expensive starting materials or starting materials of low availability. The process gives compounds with at least one five-membered cyclic monothiocarbonate group in high yield and selectivity.

Example

GC analysis: Agilent Technologies 7890 A Network GC System
Column: DB1 (Agilent) 30 m, Ø0.25 mm, film thickness 1 μm;
Carrier gas He; flow 1.0 mL/min; split ratio: 50:1
T-program: 50° C.-300° C., with ramp rate of 10° C./min; 30 min isotherm
Temperature (injection system) 250° C.

Preparation of 2-chloroethylchloroformate, Process Step b)

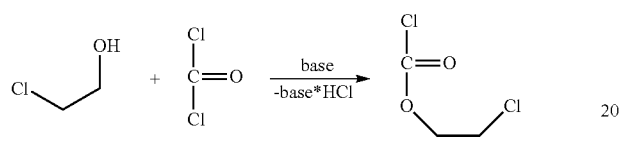

The synthesis was conducted in a 1 L stirred tank reactor equipped with two condensers (−30° C. and −78° C. (dry ice)), phosgene dip pipe, thermometer and dropping funnel. Phosgene (46.0 g, 0.5 mol) was introduced into the empty reactor at a temperature of 10° C. until a phosgene reflux was observed. Afterwards 2-chloroethanol (161 g, 2.00 mol) was added via dropping funnel over a period of 2 hours. During this time the recorded inside temperature may vary from 10 to 14° C. During the addition of 2-chloroethanol additional phosgene (404 g, 4.0 mol) was added simultaneously to ensure a phosgene reflux over the whole addition period. After complete addition of the reactants the reaction mixture was stirred at 25° C. for additional 2.5 hours and was subsequently stripped for 2 hours phosgene free with nitrogen phosgene free at 35° C. After stripping a colorless oil is obtained in high yield of 97% by weight.

Preparation of 1,3-oxathiolane-2-one, Process Step c)

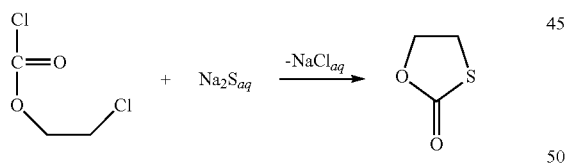

2-Chloroethylchloroformate (20 g, 0.14 mol) and dichloromethane (20 mL) were placed in a 100 mL 4 neck round bottom flask equipped with a KPG crescent stirrer, dropping funnel, thermometer and a reflux condenser. The solution was cooled down to 0° C. with an ice bath before Na$_2$S (1 eq., 15 wt % aqueous solution) was slowly added, maintaining the temperature at 5° C. After the complete addition the ice bath was removed, and the reaction mixture allowed to warm to room temperature. After stirring for 1 hour the phases were separated, and the aqueous phase was extracted with dichloromethane (3×10 mL). The solvent was removed from the combined organic phases under reduced pressure. The crude 1,3-oxathiolane-2-one was obtained with a purity of 71 area %, based on GC analysis.

Subsequent fractioned vacuum distillation at 4 mbar and an inner temperature of 60-90° C. resulted in a major fraction of the desired 1,3-oxathiolane-2-one as a clear liquid with a purity >98% (7.5 g, 51%).

The invention claimed is:
1. A process for the preparation of a compound with at least one five-membered cyclic monothiocarbonate group, the process comprising:
   a) using a compound C1 with at least one halohydrin group as starting material,
   wherein
   the compound C1 is of formula (Ia)

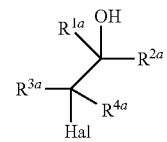

with $R^{1a}$ to $R^{4a}$ independently from each other representing hydrogen or an organic group with at maximum 50 carbon atoms, whereby, alternatively, $R^{2a}$, $R^{4a}$ and the two carbon atoms of the halohydrin group together form a five to ten membered carbon ring, and Hal representing a halide, or
wherein the compound C1 is of formula (Ib)

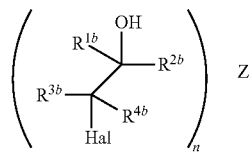

with $R^{1a}$ to $R^{4b}$ independently from each other representing hydrogen or an organic group with up to 50 carbon atoms, whereby, alternatively, $R^{2b}$, $R^{4b}$ and the two carbon atoms of the halohydrin group together form a five to ten membered carbon ring, and one of the groups $R^{1b}$ to $R^{4b}$ is a linking group to Z, Hal representing a halide, n representing an integral number of at least 2 and Z representing a n-valent organic group,
b) the compound C1 of formula (Ia) with a compound of formula (II)

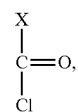

wherein
X is Cl or a group O—$R^5$ with $R^5$ representing a $C_1$-$C_4$-alkyl group, to give an adduct of formula (IIIa)

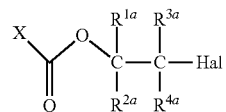

or
reacting the compound C1 of formula (Ib) with a compound of formula (II)

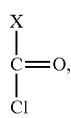

wherein
X is Cl or a group O—$R^5$ with $R^5$ representing a $C_1$-$C_4$-alkyl group, to give an adduct of formula (IIIb)

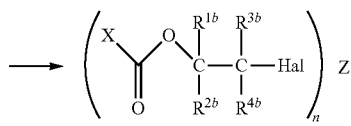

wherein $R^{1b}$ to $R^{4b}$, Z and n have the meaning above, and
c) reacting the adduct of formula (IIIa) with a compound comprising anionic sulfur to obtain the monothiocarbonate of formula (IVa)

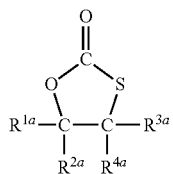

wherein $R^{1a}$ to $R^{4a}$ have the meaning above;
or
reacting the adduct of formula (IIIb) with a compound comprising anionic sulfur to obtain a compound of formula (IVb) comprising at least two cyclic monothiocarbonate groups

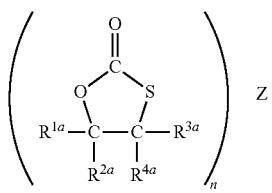

wherein $R^{1b}$ to $R^{4b}$, Z and n have the meaning above.

2. The process according to claim 1, wherein compound C1 comprises 1 to 1000 halohydrin groups.

3. The process according to claim 1, wherein at least one of $R^{1a}$ to $R^{4a}$ in formula (Ia) is not hydrogen.

4. The process according to claim 1, wherein two or three of $R^{1a}$ to $R^{4a}$ in formula (Ia) represent hydrogen, and the other groups $R^{1a}$ to $R^{4a}$ represent an organic group.

5. The process according to claim 3, wherein the groups $R^{1a}$ to $R^{4a}$ not being hydrogen represent a group $CH_2$—Cl, $CH_2$—Y—$R^6$ or $CH_2$—O—C(=O)—$R^7$ with $R^6$ and $R^7$ being an organic group with at maximum 30 carbon atoms and Y being O or S.

6. The process according to claim 1, wherein three of the groups $R^{1b}$ to $R^{4b}$ represent hydrogen, and the remaining group of $R^{1b}$ to $R^{4b}$ is the linking group to Z.

7. The process according to claim 1, wherein the linking group is a bond or a group $CH_2$— or $CH_2$—Y or $CH_2$—O—C(=O)— with Y being O or S.

8. The process according to claim 1, wherein Z is a n-valent organic group with up to 50 carbon atoms and comprises oxygen, and n is an integral number from 2 to 5.

9. The process according to claim 1, wherein n is 2.

10. The process according to claim 9, wherein Z is a polyalkoxylene group of formula (G1)

with V representing a $C_2$-$C_{20}$-alkylene group and m being an integral number of at least 1, and wherein each of the two terminal alkylene groups V is bonded to the linking group, which is one of the groups $R^{1b}$ to $R^{4b}$.

11. The process according to claim 9, wherein Z is a group of formula (G2)

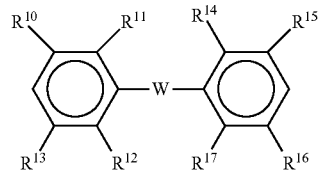

wherein
W is a bivalent organic group with at maximum 10 carbon atoms, and $R^{10}$ to $R^{17}$ independently from each other represent H or a $C_1$-$C_4$-alkyl group, and wherein the two hydrogen atoms in the para position to W are replaced by the bond to the linking group, which is one of the groups $R^{1b}$ to $R^{4b}$.

12. The process according to claim 11, wherein W is selected from the group consisting of

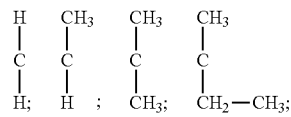

and

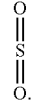

* * * * *